United States Patent [19]

Fewster

[11] Patent Number: 5,442,676
[45] Date of Patent: Aug. 15, 1995

[54] METHOD OF DETERMINING A GIVEN CHARACTERISTIC OF A MATERIAL SAMPLE

[75] Inventor: Paul F. Fewster, Brighton, England

[73] Assignee: U.S. Philips Corporation, New York, N.Y.

[21] Appl. No.: 168,732

[22] Filed: Dec. 16, 1993

[30] Foreign Application Priority Data

Dec. 21, 1992 [GB] United Kingdom ............... 9226552

[51] Int. Cl.⁶ .......................................... G01N 23/20
[52] U.S. Cl. .................................... 378/72; 378/71; 378/73; 364/508
[58] Field of Search .................. 364/490, 498, 508; 378/70, 71, 72, 72, 74

[56] References Cited

U.S. PATENT DOCUMENTS

| | | | |
|---|---|---|---|
| 4,095,103 | 6/1978 | Cohen et al. | 378/72 |
| 4,561,062 | 12/1985 | Mitchell | 364/555 |
| 4,662,222 | 5/1987 | Johnson | 73/602 |
| 4,974,209 | 11/1990 | Hoult | 364/497 |
| 5,148,458 | 9/1992 | Ruud | 378/72 |

OTHER PUBLICATIONS

"VLSI Process Modelingl—Suprem III" C. Ho et al., IEEE Transactions on Electron Devices ED-30, No. 11, 1983 pp. 1438-1453.

"A Dynamic Theory of Diffraction for a Distorted Crystal", S. Takagi ACTA Crystollographica vol. 15, 1962 pp. 1311-1312 and the Journal of Physical Society of Japan vol. 26, 1969 pp. 1239-1253.

"X-Ray Diffraction Procedures" Klug et al., John Wiley & sons, 1974, pp. 84-87, 102-115, 354-359.

"Composition and Lattice Mismatch Measurement of Thin Semiconductor Samples by X-Ray Diffraction" Fewster et al., Journal of Appplied Physics 62 (10) 15th Nov., 1987 pp. 4154-4158.

"An Expert System for X-Ray Rocking Curve Analysis" T. Tjahadi et al., International Conference '89 On "Expert Systems in Engineering Applications" Oct. 1989.

"Simulated Annealing: An Introductory Review" J. Pannetier, Neutron Scattering Data Analysis Conf. At The Rutherford Appleton, 1990 Published In Institure of Physics Conference Series No. 107, pp. 23-44.

"Multicrystal X-Ray Diffraction of Heteroepitaxial Structures", P. F. Fewster Applied Surface Science vol. 50 (1991) pp. 9-18.

"Lattice Mismatch of Simple and Comples Layer Structures by X-Ray Diffraction" P. Fewster, "Heteroepitaxial Approaches to Semiconductors: Lattice Mismatch and Its Consequences", Electrochemical Society, 1989.

Primary Examiner—Paul M. Dzierzynski
Assistant Examiner—David Vernon Bruce
Attorney, Agent, or Firm—Paul R. Miller; William L. Botjer

[57] ABSTRACT

Measurements are made on a sample ( 1 ) to obtain an experimental profile (2) having structural features (3, 4) determined at least in part by the given characteristic and an expected profile (5) calculated for the sample using selected parameters. A degree of smoothing is applied to the experimental profile (2) to reduce the structural features (3,4) thereby producing a smoothed experimental profile (21a) and the same degree of smoothing is applied to the calculated profile (5) to produce a smoothed calculated profile 51a. The smoothed calculated profile (51a) is compared with the smoothed experimental profile (21a) to determine the difference between the smoothed profiles. The calculated profile is then modified by varying at least one of the parameters until the smoothed modified profile fits the smoothed experimental profile. The above steps are then repeated with the modified calculated profile using each time a degree of smoothing less than the previous time so that the structural features return and the final modified calculated profile (5b) provides a desired fit to the experimental profile (2) thereby enabling the given characteristic to be determined from the parameters used for the final modified profile.

12 Claims, 7 Drawing Sheets

METHOD OF DETERMINING A GIVEN CHARACTERISTIC OF A MATERIAL SAMPLE

BACKGROUND OF THE INVENTION

This invention relates to a method of determining a given characteristic of a material sample such as a semiconductor material sample. In particular, but not exclusively, this invention relates to a method of determining a given characteristic, such as the strain profile of an ion implanted sample or the thicknesses or lattice mismatch between layers of a multi-layer sample using X-ray analysis techniques.

Often much information about a material sample can in principle be obtained from a profile of a given characteristic obtained by making measurements on the sample. However, in practice it can be very difficult to extract that information by making measurements directly on the experimental profile and it may be possible to extract more information by comparing the experimental profile with a calculated profile and adjusting the parameters used to obtain the calculated profile until a fit is achieved. This can prove a difficult process, especially if the experimental profile is complex and contains many peaks and troughs representing structural information.

Analysis of diffraction patterns using a probe beam such as an X-ray radiation beam has been widely used to investigate material samples, for example natural crystals and manufactured multi-layer material samples. In such analysis, an apparatus generally known as a diffractometer is used to obtain a diffraction profile by rotating a material sample relative to an incident probe beam and detecting the intensity of the beam diffracted by the sample at each angle of rotation to obtain a spectrum or profile relating the intensity of the diffracted beam to the angle of the sample. The probe beam need not necessarily be an X-ray beam but could be, for example, a gamma (g) ray radiation beam, an ultra violet radiation beam or an infra red beam or a particle beam such as a beam of neutrons or electrons. For a general explanation of X-ray analysis techniques reference may be made to many textbooks, for example "X-ray diffraction procedures" by H. P. Klug and L. E. Alexander published by John Wiley & Sons.

Generally, such X-ray diffraction profiles are complex and structural information cannot be accurately obtained simply from the experimental profile because the data represents only the intensity and not the phase of the diffracted signal and phase information is generally necessary to obtain structural information about a sample, especially if the sample is itself complex. This is explained for the case of a multilayer sample in a paper entitled "Composition and lattice mismatch measurement of thin semiconductor samples by X-ray diffraction" by P. F. Fewster and C. J. Curling published in the Journal of Applied Physics 62 (10), Nov. 15, 1987 at pages 4154 to 4158.

In the light of these problems, the approach generally adopted is to calculate a likely diffraction profile by postulating a tidal structure for the sample using, for example, information obtained from the sample preparation process, and then to compare the calculated diffraction profile with the experimental diffraction profile and to adjust the parameters determining the calculated diffraction profile by trial and error so as to refine the calculated diffraction profile until an acceptable fit is achieved between the calculated and experimental diffraction profiles, thereby indicating that the same parameters fit the experimental and the calculated diffraction profiles.

Such a procedure is extremely time-consuming and very dependent on the accuracy of the initial "guess" at the sample structure used to obtain the calculated profile which in turn is dependent on the amount and accuracy of information available about the sample structure from, for example, the sample preparation or growth process.

In addition, generally a high resolution diffraction profile such as an X-ray diffraction profile contains a wealth of information and is sensitive to many parameters which can lead to correlations between parameters and false minima making most fitting procedures (for example a least squares approach) very difficult and possibly leading to an incorrect result or more likely to an increase in the computation time required to achieve an acceptable result.

In view of the above-mentioned problems, particularly that of postulating an accurate structure from which the initial trial calculated profile is obtained, the formulation of an expert system has been proposed by T. Tjahjadi and D. K. Brown in a paper entitled "an expert system for X-ray diffraction profile analysis" presented at the International Conference '89 on "Expert Systems in Engineering Applications" held in Wuhan, China from 12th to 17th Oct., 1989 and published in the proceedings of that Conference by Huazhong University of Science and Technology Press. Although an expert system approach may well lead to improved results it requires a large amount of expenditure in time and computing power to set up an acceptable system. In addition, an expert system necessarily requires an expert knowledge base and will only be as useful or accurate as the information contained within that knowledge base. Naturally, such an expert system will only be ably to cope with problem for which it has been designed.

It is an aim of the present invention to provide a method of determining a given characteristic of a material sample which mitigates the problems mentioned above.

SUMMARY OF THE INVENTION

According to one aspect of the present invention there is provided a method of determining a given characteristic of a material sample, which method comprises
   a) making measurements on the sample to obtain an experimental profile having structural features determined at least in part by the given characteristic,
   b) calculating an expected profile for the sample using selected parameters,
   c) applying a degree of smoothing to the experimental profile to reduce the structural features thereby producing a smoothed experimental profile,
   d) applying the same degree of smoothing to the calculated profile to produce a smoothed calculated profile,
   e) comparing the smoothed calculated profile with the smoothed experimental profile to determine the difference between the smoothed calculated profile and the smoothed experimental profile,
   f) modifying the calculated profile by varying at least one of the parameters until the smoothed modified calculated profile fits the smoothed experimental profile, g) repeating steps c) to f) using each time a degree of smoothing less than the previous time so that the structural features return and the final modified calculated profile provides a desired fit to the experimental profile thereby enabling the given characteristic to be determined from the parameters used for the final modified profile.

In a second aspect, the present invention provides a method of determining a given characteristic of a material sample by X-ray analysis, which method comprises a) making X-ray measurements on the sample to obtain an experimental X-ray diffraction profile determined at least in part by the given characteristic, b) calculating an expected X-ray diffraction profile for the sample using selected parameters, c) applying a degree of smoothing to the experimental profile to reduce the structural features thereby producing a smoothed experimental profile, d) applying the same degree of smoothing to the calculated profile to produce a smoothed calculated profile, e) comparing the smoothed calculated profile with the smoothed experimental profile to determine the difference between the smoothed calculated profile and the smoothed experimental profile, f) modifying the calculated profile by varying at least one of the parameters until the smoothed modified calculated profile fits the smoothed experimental profile, g) repeating steps c) to f) using each time a degree of smoothing less than the previous time so that the structural features return and the final modified calculated profile provides a desired fit to the experimental profile thereby enabling the given characteristic to be determined from the parameters used for the final modified profile.

Thus, by using a method in accordance with the invention the experimental and calculated profiles are both smoothed so as to reduce subsidiary structural features in the profiles. This smoothing allows a first fit to be achieved by adjusting the parameters affecting the smoothed calculated curve relatively quickly giving a more accurate calculated curve. The smoothing steps are then repeated using the more accurate calculated profile and the comparing and fitting procedure again carried out to produce an even more accurate calculated profile. These steps are repeated until the structural features return to the experimental profile sufficiently to enable a fit of the calculated profile and of the desired accuracy to be achieved. Depending upon the particular circumstances, the degree of smoothing may be reduced to zero or may become insignificant. The final calculated profile is compared with the experimental profile and the final adjustments made to the calculation parameters to achieve a desired fit. Thus no attempt is made to compare the detail of the initial "guess" at the structure with the detail of the experimental profile; rather a smoothed version of the initial guess is compared with a similarly smoothed experimental profile and the degree of accuracy of the fitting procedure is increased by reducing the degree of smoothing each time the calculated profile is improved. This should generally reduce the computation time required for the fitting procedure, especially if the initial guess is not close, because time is not wasted in trying to fit the detail of an inaccurate calculated curve to the detail of the experimental curve. In addition, the smoothing of the experimental and calculated profiles removes or at least reduces the possibility of satellite or false minima occurring in the fitting procedure which would otherwise increase the possibility of a false result or at a minimum cause an unnecessary increase in computation time.

In addition, the effect of noise, that is unwanted extraneous signals, in the experimental profile should be reduced because the noise is smoothed out during the fitting procedure and so should not adversely affect the fitting of the calculated to the experimental profile. Furthermore, in contrast to the expert system described above, this method is not restricted to a particular situation nor is it reliant on the accuracy and completeness of data in an expert system data store.

The measurements on the sample are preferably made by using a diffraction probe beam such as an X-ray, X-ray, infra red or ultra violet radiation beam or a particle beam such as a neutron or electron beam to obtain an experimental diffraction profile which has the advantage of being a non-destructive technique.

Preferably, the experimental and calculated profiles are smoothed by convoluting the experimental and calculated profiles separately with a smoothing profile having a given base width and step g) is carried out by reducing the base width of the smoothing profile each time steps c) to f) are repeated. This has the advantage that it is not necessary to understand the physical interactions as is the case for an expert system approach. Such a smoothing technique can be likened to simulating a thermal annealing of the sample, that is to simulating the changes which would occur if the sample temperature were increased, and the effective temperature reduced each time steps c) to f) are repeated. Such a smoothing procedure is particularly advantageous because it mimics the changes: in the actual structure which arise with an increase in the thermal energy of the component atoms or molecules and therefore does not impose any artificial features onto the profiles. For general information on the technique of simulated annealing, reference may be made to, for example, the book entitled "Simulated annealing: Theory and Applications" by P. J. M. van Laarhoven et. al. published by D. Reidel Publishing Company or diverse papers, for example "Simulated annealing: an introductory review" by J. Pannetier presented at the Neutron Scattering Data Analysis Conference at the Rutherford Application, 1990 published in the Institute of Physics Conference Series No. 107, Chapter 1 at pages 23 to 44.

The smoothing profile may have any suitable shape, for example a Gaussian or rectangular shape, however the use of a triangular shape smoothing profile makes the convolution process relatively simple and keeps computation time low.

Dependent upon the particular profile, in particular on the proximity to the structural features of interest of extraneous or subsidiary features, the smoothing profile may be reduced to a delta function so that, at the final comparing step, the original experimental profile is compared with the modified calculated profile.

The experimental and calculated profiles may be provided as normalised logarithmic profiles which should be of assistance in connection with the dynamic range and the determination of the difference between the experimental and calculated profiles which may be obtained by comparing the profiles by determining the difference between corresponding points of the two profiles and summing these differences for a number of points to determine an error value for the difference between the experimental and calculated profiles. Step f) may be carried out each time by 1) varying the parameters in turn to determine which parameter causes the largest change in the difference between the experimental and calculated profiles, 2) varying that selected parameter until the change in the difference between the experimental and calculated profiles caused by varying that parameter reaches a predetermined limit, 3) storing the changed value of the selected parameter and repeating steps 1) to 3) for each parameter using the changed value of the selected parameter until a desired fit between the experimental and calculated profiles is achieved. Such a procedure is very simple and may be particularly advantageous where there is a strong correlation between the parameters.

A method in accordance with the invention may be used basically to, for example, determine strain and scattering as a function of layer thickness. Thus a method in accordance with the invention may be used, for example, to determine the strain profile of an ion-implanted semiconductor sample, to determine the lattice mismatch between or composition of different layers of a multi-layer material sample or to determine the thicknesses of the layers of a multi-layer material sample.

BRIEF DESCRIPTION OF THE DRAWING

Embodiments of the present invention will now be described, by way of example, with reference to the accompanying; drawings, in which.

DETAILED DESCRIPTION OF THE PREFERRED EMBODIMENTS

Figure 1:
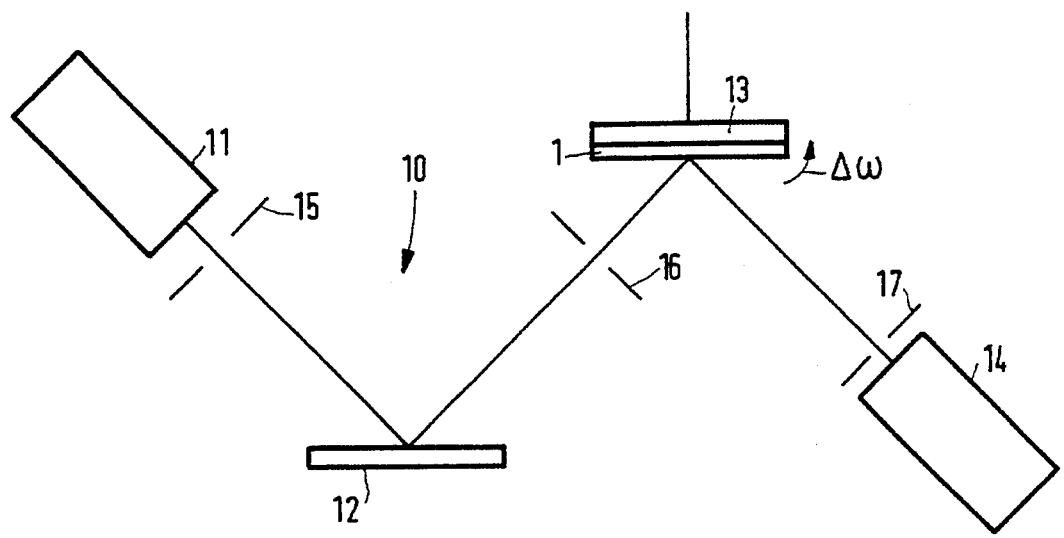
FIG. 1 shows a very schematic outline of a diffractometer for obtaining an experimental curve for use in a method in accordance with the invention.

Referring now to the drawings, there is illustrated a method of determining a given characteristic of a material sample 1, which method comprises a) making measurements on the sample 1 to obtain an experimental profile 2 having structural features 3, 4 determined at least in part by the given characteristic, b) calculating an expected profile 5 for the sample using selected parameters, c) applying a degree of smoothing to the experimental profile 2 to reduce the structural features 3,4 thereby producing a smoothed experimental profile 21a, d) applying the same degree of smoothing to the calculated profile 5 to produce a smoothed calculated profile 51a, e) comparing the smoothed calculated profile 51a with the smoothed experimental profile 21a to determine the difference between the smoothed calculated profile 51a and the smoothed experimental profile 21a, f) modifying the calculated profile by varying at least one of the parameters until the smoothed modified profile fits the smoothed experimental profile 21a, g) repeating steps c) to f) using each time a degree of smoothing less than the previous time so that the structural features return and the final modified calculated profile 5b provides a desired fit to the experimental profile 2 thereby enabling the given characteristic to be determined from the parameters used for the final modified profile.

Thus, by using a method in accordance with the invention the experimental and calculated profiles 2 and 5 are both smoothed so as to reduce subsidiary structural features in the profiles. This smoothing allows a first fit to be achieved by adjusting the parameters affecting the smoothed calculated profile or curve 51a relatively quickly giving a more accurate calculated curve. The smoothing steps are then repeated using the more accurate calculated profile and the comparing and fitting procedure again carried out to produce an even more accurate calculated profile. These steps are repeated until the structural features return to the experimental profile sufficiently to able a fit of the calculated profile to the experimental profile 2 of the desired accuracy to be achieved. Depending upon the particular circumstances, the degree of smoothing may be reduced to zero or may become insignificant, and the final calculated profile compacted with the original experimental profile and the final adjustments made to the calculation parameters to achieve a desired fit. Thus no attempt is made to compare the detail of the initial "guess" at the structure with the detail of the experimental profile; rather a smoothed version of the initial guess is compared with a similarly smoothed experimental profile and the degree of accuracy of the fitting procedure is increased by reducing the degree of smoothing each time the calculated profile is improved. This should generally reduce the computation time required for the fitting procedure, especially if the initial guess is not close, because time is not wasted in trying to fit the detail of an inaccurate calculated curve to the detail of the experimental curve. In addition, the smoothing of the experimental and calculated profiles removes or at least reduces the possibility of satellite or false minima occurring in the fitting procedure which would otherwise increase the possibility of a false result or at a minimum cause an unnecessary increase in computation time.

In addition, the effect of noise, that is unwanted extraneous signals, in the experimental profile should be reduced because the noise is smoothed out during the fitting procedure and so should not adversely affect the fitting of the calculated to the experimental profile. Furthermore, in contrast to the expert system described above, this method is not restricted to a particular situation nor is it reliant on the accuracy and completeness of data in an expert system data store.

Referring now specifically to the drawings, FIG. 1 illustrates very schematically a diffractometer 10 for use in obtaining an experimental diffraction profile 2. Although in this example the diffractometer is an X-ray diffractometer using an X-ray beam as a diffraction probe beam, the method to be described could be applied to the situation where the diffractometer provides a different sort of diffraction probe beam, for example an γ-ray, infra red or ultra violet radiation beam or a neutron or electron particle beam, depending upon the particular nature of the sample being analyzed and the information desired to obtained from the sample.

In this example, the diffractometer 10 comprises a source 11 of K series X-ray radiation derived from a suitable target such as a copper target, a suitable monochromator 12 for defining a monochromatic X-ray beam X, generally a $K\alpha$ beam, a sample holder 13 for carrying a sample 1 to be measured and a detector 14 for detecting X-ray radiation diffracted by the sample 1. As is conventional a divergence slit 15 may be placed immediately after the source 11, a scatter slit 16 positioned as appropriate in the radiation path and an acceptance slit 17 positioned in front of the detector 14. In the example shown, the monochromator is positioned as a primary monochromator (that is between the source 11 and the sample 1 ), however it could be positioned as a secondary monochromator after the sample 1.

Although the monochromator is shown as a single reflection monochromator any suitable form of monochromator 12 and detector 14 may be used. To give an example, the diffractometer may be a commercially available diffractometer such as the Philips High Resolution X-Ray Diffraction (HR-XRD) system MPD 1880/HR sold by Philips Electronics NV of the Netherlands which has a two-crystal, four-reflection monochromator. Also, the method to be described could be used with a very simple X-ray diffractometer which consists merely of a source, slit, sample and detector.

Any suitable procedure may be used to obtain the experimental diffraction profile 2. In this example the sample 1, in this case an ion-implanted single crystal silicon sample, is mounted to the sample holder 13 which is then rotated in a conventional stepwise manner about an axis parallel to the desired diffraction plane, as illustrated in FIG. 1, through an angle encompassing a particular strong sample reflection, for example the 004 reflection, and the X-ray radiation diffracted from the sample is detected and recorded at each step. The detected X-ray intensities are plotted against the angle of rotation $\Delta\omega$ measured from the normal to the diffraction plane of the sample 1. Such an X-ray diffraction profile is known as a rocking curve. Other measurement procedures where, for example, the detector 14 and the sample 1 are both rotated about the same axis, for example an $\omega-2\omega'$ scan as described in, for example, a paper entitled "Multicrystal X-ray diffraction of heteroepitaxial structures" by P. F. Fewster published in Applied Surface Science Volume 50 (1991) at pages 9 to 18, may be used to produce the experimental X-ray diffraction profile.

Figure 2:
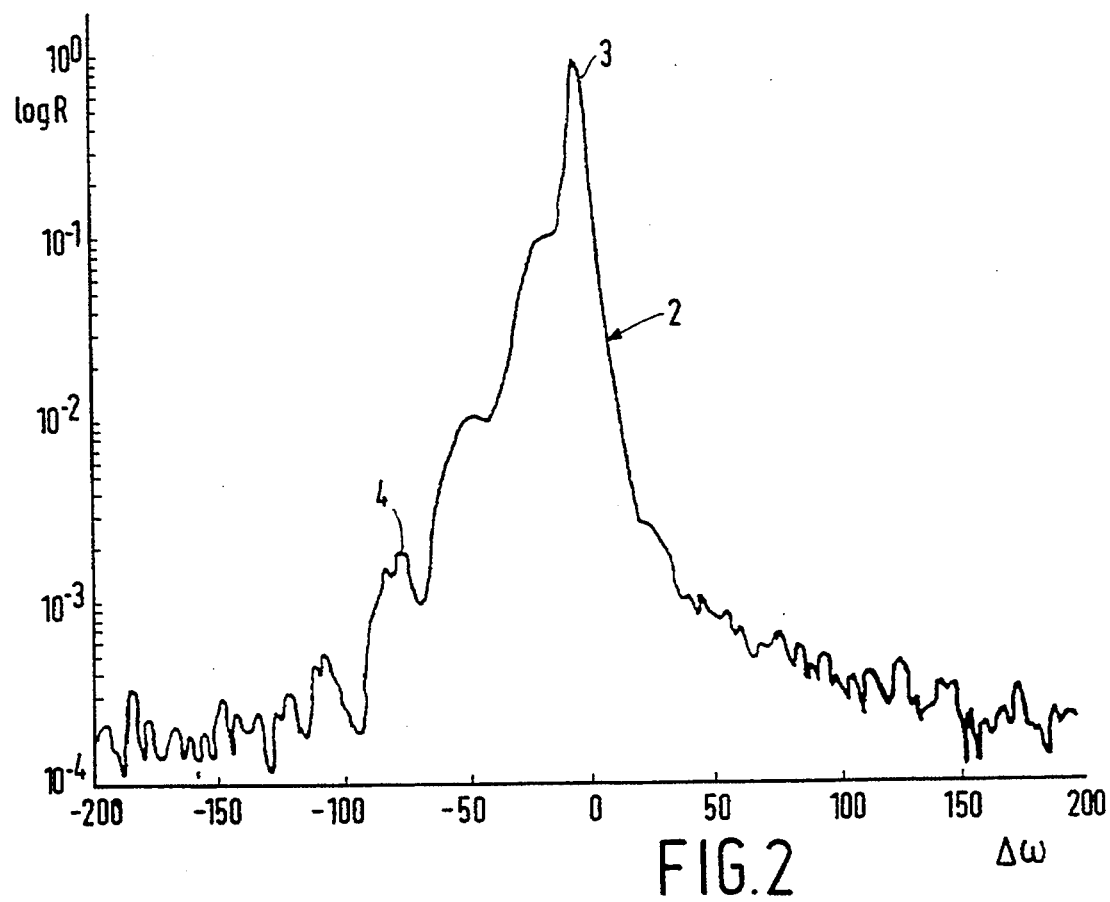
FIG. 2 illustrates schematically the profile of an experimental 004 reflection X-ray diffraction profile obtained from a given material sample.

FIG. 2 shows a typical experimental X-ray diffraction profile 2 in which the logarithm of the reflectivity log R of the sample (the intensity of the diffracted beam is normalised in this example so that the signal for the most intense peak is 1; however any suitable normalization factor may be used) plotted against the change $\Delta\omega$ in arcseconds in the angle of the sample surface away from the strong 004 reflection.

The experimental X-ray diffraction profile 2 has of course structural features and contains much structural information which can, however, only be extracted satisfactorily by fitting the experimental curve or profile 2 to a calculated curve or profile 5 because of the lack of phase information in the intensity signals. In the case shown in FIG. 2, the structural features consist of a main peak 3 and many subsidiary peaks and troughs 4; however, as is known by those skilled in the art, an experimental diffraction profile may have several main peaks and divers forms of subsidiary features.

In this case, a method in accordance with the invention is to be used to enable parameters relating to the strain profile of an ion-implanted semiconductor to be determined. In order to enable calculation of a likely diffraction profile 5 for such a sample, it is necessary to postulate a likely strain profile for the sample. There are several views amongst those skilled in the art about the parameters which affect the strain profile. The present inventor believes that it is affected by several distributions.

Thus, the dopant atoms remaining at interstitial sites cause a linearly related expansional lattice strain, and displaced lattice atoms, silicon self-interstitials, cause an expansional lattice strain lineady related to $\Phi.F_d$ where $\Phi$ is the flux of implanted ions in ions/cm$^2$ and $F_d$ the energy per incident ion per unit depth deposited in nuclear interactions. A vacancy distribution produced by the ion implantation is similarly linearly related to $\Phi.F_d$ and a strain, compressive where the dopant is boron or phosphorus, resulting from the dopant atoms becoming substitutional after annealing of the sample, is linearly related to the dopant concentration profile. All of the above should be taken into account in the calculation of the diffraction profile 5. However in the example to be described the sample under analysis has not yet been annealed and accordingly the affect on the strain profile of the annealing step can be ignored in this case. Similarly, as the strain caused by interstitial atoms is about one order of magnitude higher than that caused by vacancies, the effect of the latter can be ignored.

Any suitable method may be used to calculate the strain profile and, as a starting point, here the dopant profile which is lineady related to the strain profile is used. It is assumed that the strain is confined to the direction perpendicular to the sample surface. Thus, for example, the dopant concentration profile may be calculated using a suitable computer simulation such as SUPREM III (see for example the paper by C. Ho et. al. in IEEE Transactions on Electron Devices ED-30, 1983 at pages 1438 to 1453). This gives a Pearson IV dopant distribution determined by five parameters. However, for ease of calculation, a two-sided Gaussian dopant profile determined by only four parameters is used here to approximate the strain distribution. The strain $St = \Delta d/d$, where d is the lattice parameter, is thus given by:

$$\frac{\Delta d}{d} = \tau \cdot e^{-(\frac{x-\rho}{2\sigma_i})^2} \quad \begin{array}{l} i = 1 \text{ for } x \leq \rho \\ i = 2 \text{ for } x > \rho \end{array} \quad (1)$$

where $\rho$ is the implanted range; $\sigma_1$ is the variance (straggle) for depth smaller than $\rho$, $\sigma_2$ is the variance for depth greater than $\rho$ and $\tau$ is the peak or maximum strain.

Figure 3:
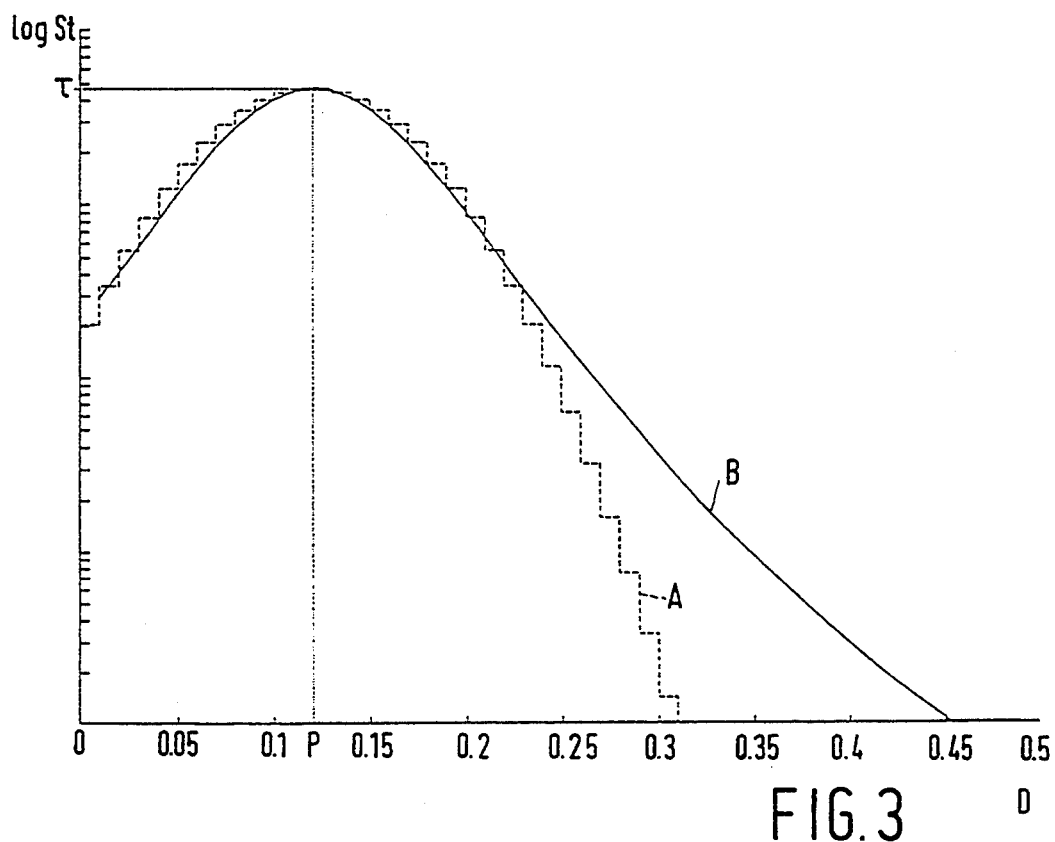
FIGS. 3 illustrates schematically calculated strain profiles for a material sample being analyzed.

FIG. 3 which plots strain St in arbitrary units against depth D in microns shows in dashed lines the thus derived Gaussian dopant profile A fitted to the calculated Pearson IV profile B. Other possible functions could be used to calculate the dopant profile for example a two-sided exponential or a two-sided Lorentzian function.

Figure 4:
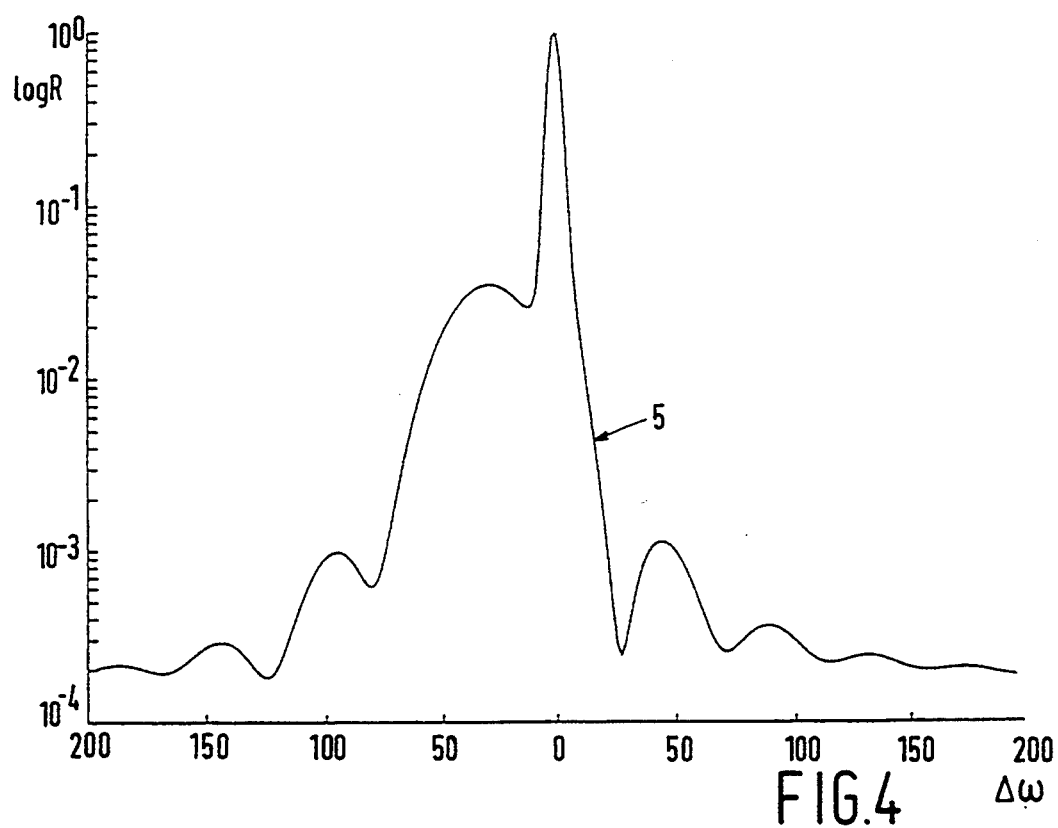
FIG. 4 illustrates the calculated 004 reflection X-ray rocking profile obtained for the given sample using the strain profile shown in FIG. 3.

In this example the thus calculated strain profile St is used together with the dynamical theory of X-ray diffraction as described by, for example, S. Tagaki in Acta Crystollographica Volume 15,1962 at pages 1311 to 1312 and the Journal of the Physical Society of Japan Volume 26, 1969 at pages 1239 to 1253 to determine a suitable calculated X-ray diffraction profile for use in the fitting procedure. The kinematical or semi-kinematical theory could possibly be used, however it is generally necessary to use a dynamical approach as explained in the Journal of Applied Physics volume 62, 1987 at pages 4154 to 4158 by P. F. Fewster and C. J. Curling. A background level, determined experimentally, may be included to account for the practical dynamic range and generally the calculated profile 5 will involve a convolution with an appropriate function to account for instrument broadening of the diffraction peaks. In the above-mentioned example, for simplicity the convolution used is a Gaussian with a Full Width at Half Maximum (FWHM) of 4.7 arcseconds; however the true instrument profile could be used. The calculated profile 5 is normalised in the same way as the experimental profile 2. FIG. 4 is a graph similar to FIG. 2 but illustrating the calculated X-ray diffraction profile 5.

Having thus obtained the experimental diffraction profile 2 and the calculated diffraction profile 5, the calculated diffraction profile 5 has then to be fitted to the experimental diffraction profile 2. This process will now be described with reference to FIG. 5 which illustrates a suitable smoothing or annealing profile S, FIG. 6 which shows the effect of the smoothing or annealing process on an X-ray diffraction profile and FIG. 7 which is a very schematic rudimentary flowchart for illustrating the fitting of the calculated diffraction profile 5 to the experimental diffraction profile 2.

Thus, initially, a smoothing or annealing profile S is selected which, when convoluted with a diffraction profile, smooths out or reduces the peaks and troughs in the profile Such a smoothing technique can be likened to simulating a thermal annealing of the sample, that is to simulating the changes which would occur if the sample temperature were increased.

Figure 5:
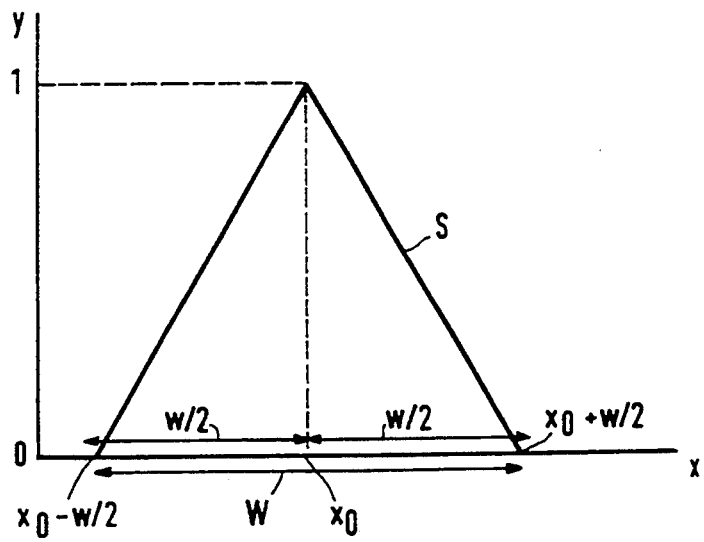
FIG. 5 illustrates schematically a smoothing or annealing profile.

In this case, as shown in FIG. 5, the annealing profile S has a triangular form:

$$x < (x_o - W/2) \quad y = 0$$
$$(x_o - W/2) < x < x_o \quad y = 2/W(x - (x_o - W/2))$$
$$x_o < x < (x_o + W/2) \quad y = -2/W(x + (x_o - W/2))$$
$$x > (x_o + W/2) \quad y = 0$$

where x and y are the ordinate and abscissa coordinates, respectively, in FIG. 5, $x_o$ is a given value of x as indicated in FIG. 5 and W is the base width of the triangle. Such a smoothing profile S has advantages in that it is easy to calculate, goes to zero outside the desired range, unlike profiles such as Gaussian profiles, does not detrimentally affect the dynamic range and is defined simply by the base width W. Other smoothing profiles could be used such as the Gaussian mentioned above or a rectangular profile, although they could distort the shape of the profile being smoothed.

As is well known from many textbooks on convolution theory, the convolution of two functions f(x) and g(x) is defined as:

$$C(x) = f(u)g(x-u)du$$

and effectively this process involves multiplying each point of one function by the other function.

Figure 6:
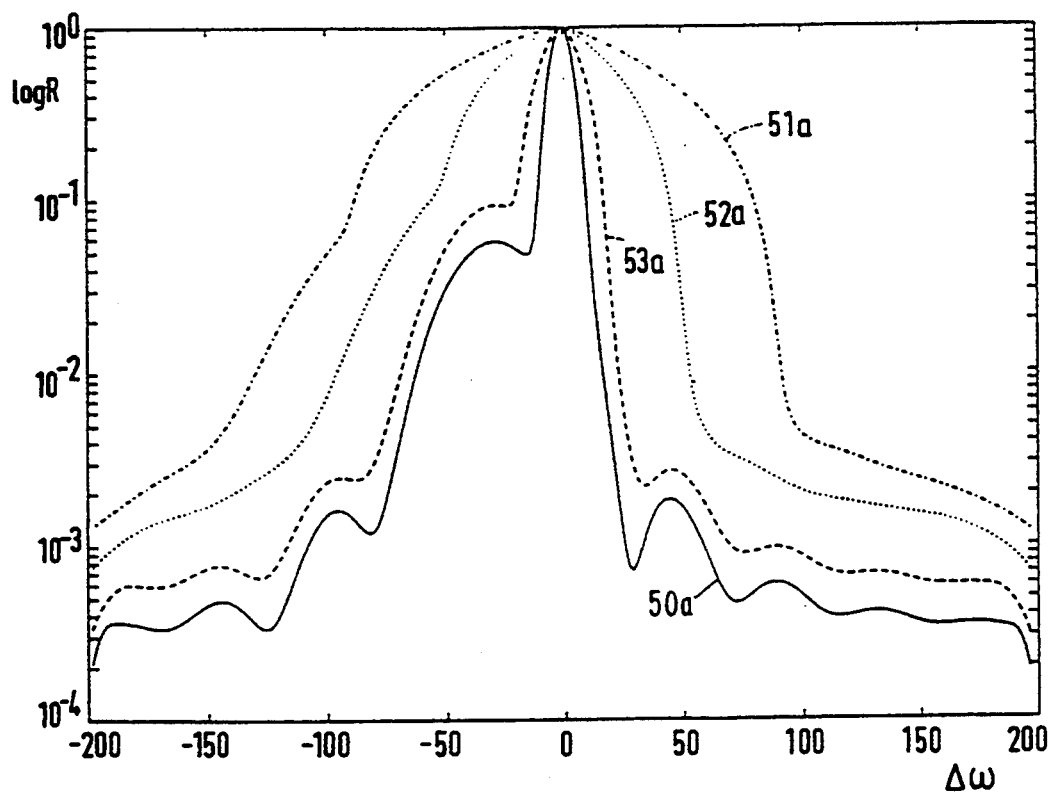
FIG. 6 illustrates graphically the effect of smoothing by simulated annealing on an X-ray diffraction profile similar to those shown in FIGS. 2 and 4.

FIG. 6 illustrates the effect of convoluting a diffraction profile (as shown the calculated diffraction profile 5 but it could equally be the experimental diffraction profile 2) with the smoothing function or profile S for different values of the base width W. As will be appreciated, the narrower the base W (in arcseconds) of the tangle the smaller the degree of smoothing of the diffraction profile which results from the convolution process.

It will of course be appreciated that the smoothed profiles shown in FIG. 6 are only representational and do not necessarily illustrate sequential steps in the fitting procedure. Moreover, although only three smoothed profiles are shown, there may be many more. The profiles shown in FIG. 6 are labelled as 5na where n is an integer indicating the smoothing step, that is so that the first (n=1) smoothed profile is labelled as 51 a, the second (n=2) as 52a and so on with the unsmoothed or original profile (n=zero) being labelled, as indicated previously, as 5. A similar identification may be adopted for the experimental smoothed profiles.

As can be seen from FIG. 6, the first smoothing step convolutes the experimental and calculated diffraction profiles 2a and 5 with a triangular function S having a base width W sufficient to remove; all but the main peak 3, that is so that all subsidiary peaks and troughs are smoothed out. The actual base width W of the triangular function S required to achieve this will of course depend on the complexity of the diffraction profiles being compared and will generally be determined by computations on a tidal and error basis until the computer program used ascertains that the minimum degree of smoothing (that is the minimum simulated annealing temperature) required to smooth out all subsidiary features of the profiles has been applied. As is cleary shown in FIG. 6 as the degree of smoothing, that is as the base width W, is reduced more and more of the structural features of the original profile 5 reappear.

Figure 7:
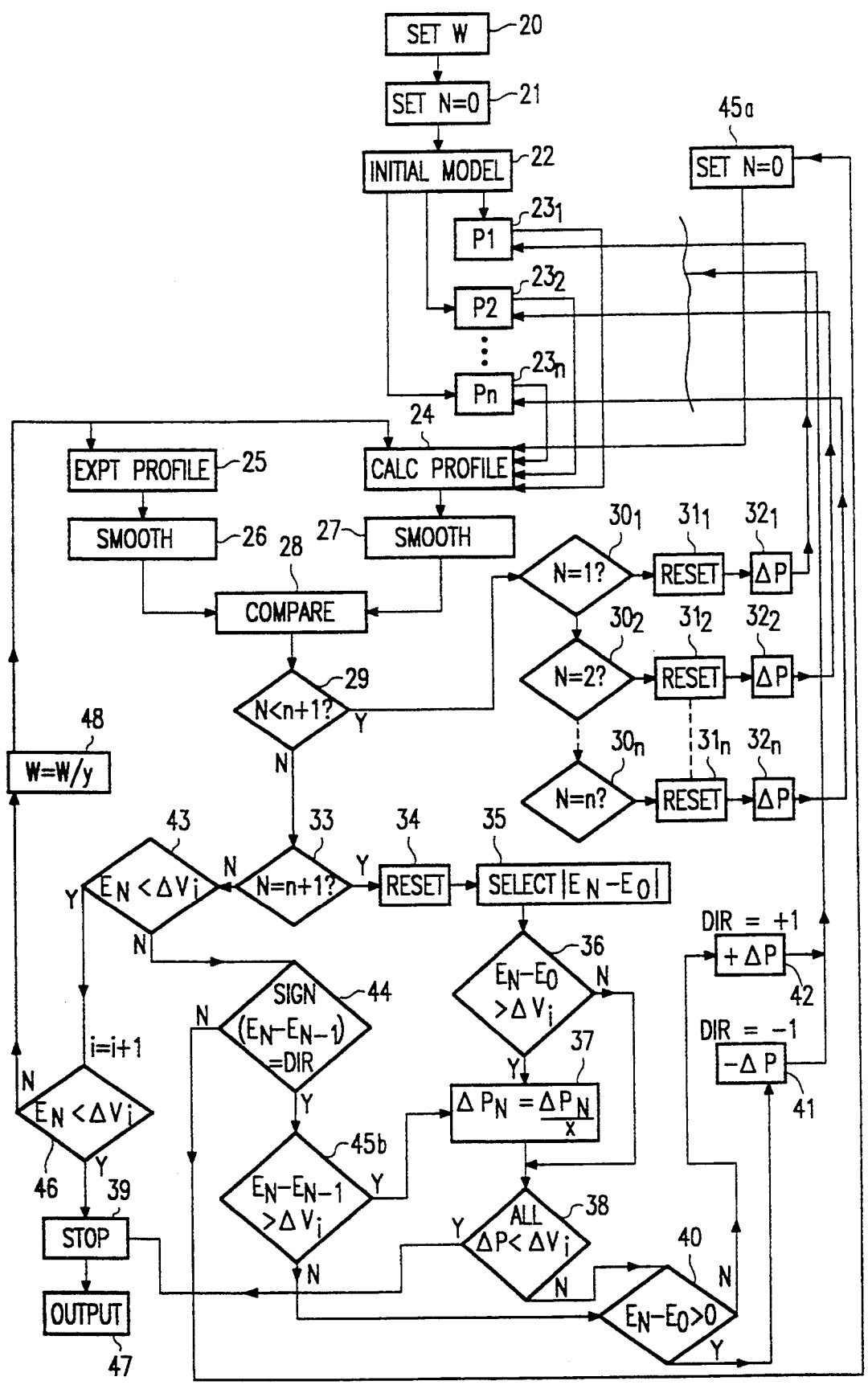
FIG. 7 illustrates a very schematic flow chart for a method in accordance with the invention.

Generally, the fitting procedure will be carried out using a computer programmed using conventional techniques to follow an algorithm which is now to be described with the help of FIG. 7.

Thus, first the initial conditions are set, that is an initial value for the base width W is selected as indicated at box 20 and a variable N is set to zero as indicated at box 21, for the initial model (box 22) which is determined as discussed above and for which initial values of parameters P1 to Pn are used, as indicated by boxes $23_1$ to $23_n$ (where n indicates the number of parameters), to calculated the likely profile, that is to determine the initial calculated profile 5, as indicated by box 24.

Assuming the measured or experimental diffraction profile 2 is already stored in the computer as represented by the box 25 in FIG. 7, the experimental and calculated diffraction profiles 2 and 5 are separately convoluted with the initial smoothing profile S (which has the base width W set at box 20) as indicated by steps or boxes 26 and 27, respectively, in FIG. 7 to produce smoothed experimental and calculated diffraction profiles 21 a and 51 a.

These smoothed profiles 21a and 51a are then compared at step 28 using an appropriate technique in which each point of the smoothed calculated diffraction profile 51 a is compared with the corresponding point of the smoothed experimental diffraction profile 2a. The errors or differences between the smoothed experimental and smoothed calculated profiles 21a and 51a are then summed to determine the overall error in accordance with the following equation:

$$E(\sigma_1,\sigma_2,\rho,\tau) = \sum_{\omega} |\log(R_m(\omega)) - \log(R_c(\omega,\sigma_1,\sigma_2,\rho,\tau))| \quad (2)$$

where $R_m$ is the measured and $R_c$ the calculated reflectivity.

There are a number of other possibilities for determining the error but the above approach was found to be particularly effective.

The overall error E is stored as indicated at step 28. As indicated by decision box 29, if N is less than n+1 (where n is the number of different parameters P) then as indicated by a series of decision boxes $30_1$ to $30_n$, a determination is made as to the current value of N and the corresponding parameter (that is P where N=I) is adjusted (after having reset the parameters to their original values at boxes 31) by a predetermined amount $\Delta P$ as indicated by the corresponding box $32_N$ and the adjusted value of the parameter then used to recalculate the calculated profile which is then resmoothed and recompared with the experimental profile 2 to determine the new error value $E_N$. This procedure is repeated for each of the parameters P in turn, that is until N=n+1 as indicated by the decision box 33.

The value of the last parameter $P_n$ is then reset at step 34 and the various new error values $E_N$ compared with the original error value $E_o$ to determine at step 35 the parameter for which the change AP had most effect on the error value, that is the parameter $P_N$ for which $|E_N-E_O|$ is greatest. This parameter is then selected for adjustment. If as indicated by decision box 36, the difference between the original error value $E_o$ and the new error value $E_N$ is greater than a predetermined minimum acceptable value $\Delta V_i$, where is like N an iterant which is altered each time a step is repeated, (normally selected by trial and error and determined at least in part by the characteristics of the sample;) as indicated by decision box 36, then as illustrated at step 37, the value of the change $\Delta P$ in the selected parameter is altered so that zP becomes equal to $\Delta P/x$ where x is a selected value greater than one. A check is then made at step 38 to see if all the values of the changes in the parameters $\Delta P_N$ are all less than AV. The same check is made at step 38, if as indicated by decision box 36, the difference between the original error value $E_O$ and the new error value $E_N$ is less than the predetermined minimum acceptable value $\Delta V_i$. If the answer to this question is yes, then the program will be stopped as indicated at box 39 because the best fit will have been achieved. Flowever, at this stage in the fitting procedure, the more likely answer is no so that the procedure moves onto step 40 which determines whether the difference $(E_N-E_O)$ is greater than zero. If the answer is yes, the difference is greater than zero, that is DIR=-1, then the selected parameter $P_N$ is changed by $-\Delta P$ (box 41 ). However, if the answer is no, the difference is less than zero, that is DIR= +1, then the selected parameter $P_N$ is changed by $+\Delta P$ (box 42). The changed value of the selected parameter $P_N$ is then used to recalculate the calculated profile and the above-described procedure is repeated until a determination is made at step 33 that the value of N is greater than n+1.

A determination is then made at step 43 as to whether $E_N$ is less than $zV_i$. If the answer is no, then a determination is made at box 44 as to whether the sign of the difference $(E_N-E_{N-1})$ is DIR, that is whether it is still the same. If it is not and it has therefore reversed indicating that the minimum error has probably been passed, then N is set equal to zero at box 45a, the profile recalculated at step 24 and resmoothed at box 27 for comparison and fitting with the experimental profile 2 as discussed above. If, however, the sign of the difference $(E_N-E_{N-1})$ is still the same and is greater than $\Delta V_i$ (box 45b), then the program returns to box 37 where the change $\Delta P$ is again altered. If the difference $(E_N-E_{N-1})$ is not greater than $\Delta V_i$ (box 45b), then $\Delta P$ is not changed, rather the program proceeds directly to step 40.

If the value of $E_N$ is less than $\Delta V_i$ (box 43), then the iterant iis increased to i=i+1, effectively reducing the value of $\Delta V$ by a predetermined selected amount, and a determination made at box 46 as to whether $E_N$ is less than $\Delta V_i$. If the answer is yes then the best fit has been achieved and the procedure is stopped (box 39) and the final parameters which give the best fit are output (box 47). More likely, the answer is no and the value of W is then set at box 48 to W/y where y is a predetermined selected value greater than one, that is the width W of the smoothing profile S is reduced. This new reduced value of W is then supplied back to boxes 25 and 24 and used for alB subsequent smoothing steps. Each time box 48 is encountered the value of W is again reduced and the degree of smoothing thus reduced and the fitting procedure described above repeated until $E_N$ is less than the current value of $\Delta V_i$ when the procedure is stopped and the current parameters output (box 47) as being those which provide the calculated profile 5b having the best fit to the experimental profile 2.

It should of course be appreciated the degrees or amounts by which the variables $\Delta P$, $\Delta V$, W, etc. are changed each time will generally be determined by trial and errorto be those values of change most appropriate for the sample in question.

It will be appreciated by those skilled in the art that there are many sophisticated parameter optimization techniques currently available and that any one of these could have been used. However, the very simple fitting procedure used in the above described example was found to be particularly acceptable. As will have been appreciated from the above, the four parameters mentioned above which affect the Gaussian strain profile, namely $\sigma_1$, $\sigma_2$, $\rho$ and $\tau$ are varied one by one with a certain step size which is generally selected by trial and error and may be for example 10% (percent). The parameter which causes the largest change in the difference or error between the smoothed calculated and experimental curve profiles 21a and 51a is selected. The selected parameter is then adjusted in a step-wise manner with at each step the calculated curve being recalculated for the adjusted parameter, resmoothed using the same smoothing step S and then compared with the smoothed experimental profile 21a. As the difference between the experimental and calculated curve profiles reduces, the size of the step change in the selected parameter is reduced. This procedure is continued until the step or change in the parameter reaches a preselected minimum value. At this stage the selected parameter is maintained at its then adjusted value and another one of the parameters is adjusted.

This process is carried out for each (four in this case) parameter in turn until the step size change for each parameter reaches a preselected minimum value, at which stage the adjusted smoothed calculated profile 51b is deemed to fit the smoothed experimental profile 21a and the adjusted calculated profile is stored. This approach is equivalent to the so-called steepest descent method and has advantages in this particular case because it prevents the parameters drifting away from their optimum values because there is a strong correlation between the parameters. Of course, the fitting procedure which is most appropriate in this case may not necessarily be the most suitable for another situation and the fitting procedure should be selected according to the particular circumstances.

The stored profile calculated using the newly found parameters is then used for the subsequent smoothing step. The fact that this is not the first smoothing step is identified and the smoothing profile is adjusted by reducing the base width W of the triangular smoothing profile, thereby reducing the effective temperature of the simulated anneal.

As indicated above, the actual size of the step change in the base width W will generally be determined by trial and error and may, like the change in the selected parameter, be reduced with progressive smoothing steps so that the step change is not uniform. The second smoothed experimental and calculated profiles are then compared as before and the same fitting procedure carried out, after which the further modified calculated profile is supplied to the subsequent smoothing procedure in place of the modified calculated profile. This process of smoothing, comparing and then adjusting the calculated profile until it fits the experimental profile is repeated with each time the degree of smoothing, that is the effective annealing temperature, being reduced until the degree of smoothing is generally zero or sufficiently small to allow an acceptable fit of the calculated profile to the experimental profile. Thus, when the modified calculated profile no longer changes by more than a selected minimum amount, the final modified calculated profile 5b is deemed to fit the experimental profile, the fitting procedure is brought to an end and the parameters used for the calculated profile can be considered valid for the experimental profile 2.

The strain profile of the ion-implanted sample under test can thus be determined and the information used to, for example, provide a quality check to ensure that each one of a batch of samples has the same strain profile or to enable adjustments to be made in the ion-implantation process so as to optimise the strain profile for certain characteristics. Such information may also be used to determine the depth of pn junctions and the location of defects which information can be valuable in determining the electrical properties of the device and can, for example, be used to assess which samples from a production run meet desired quality criteria or to assist in the optimisation of the method of manufacture, by for example using the information to adjust implantation processes annealing procedures etc., of devices which are to have articular characteristics.

Figure 8:
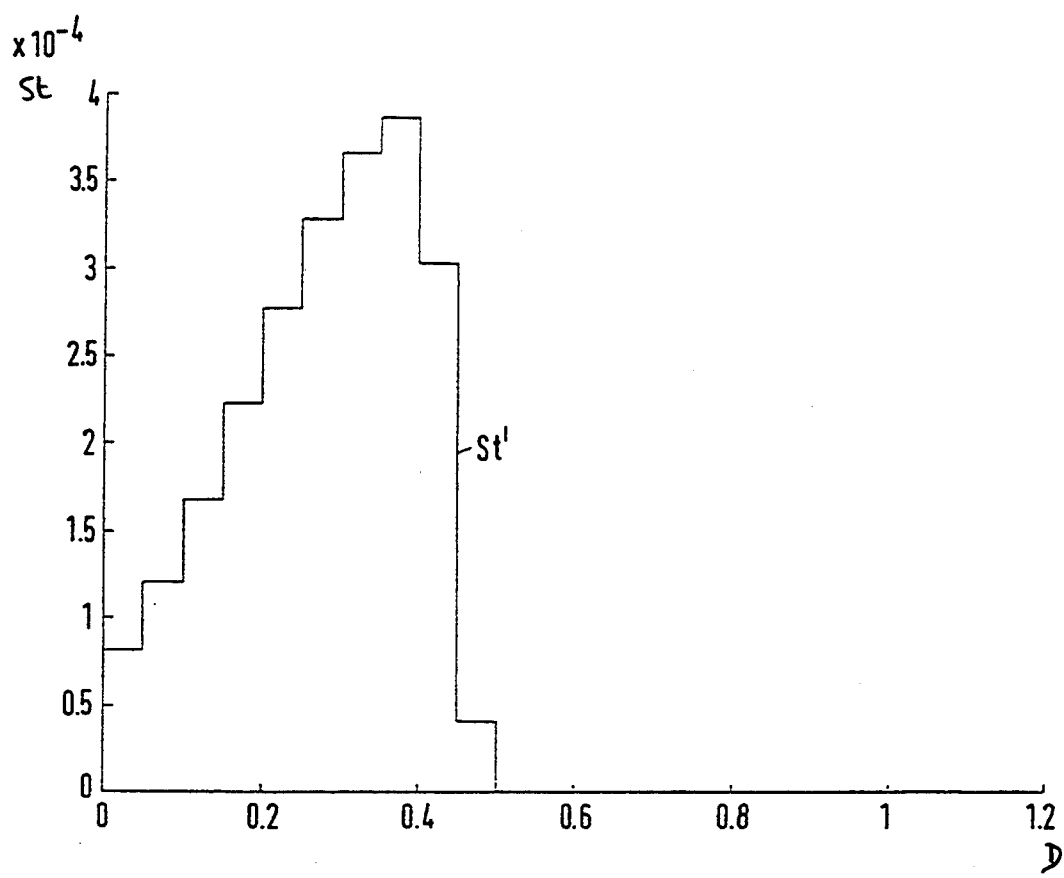
FIG. 8 illustrates a calculated strain profile intended to represent a likely profile for an actual sample for testing the viability of the method.

FIG. 8 is a graph similar to FIG. 3 illustrating an arbitrarily chosen Gaussian strain profile St. This strain profile St is used to calculate an X-ray diffraction profile similar to FIG. 2 to form an artificial experimental X-ray diffraction profile which can be compared with a calculated profile 5 to test the viability of the method described above in FIG. 8 the parameters have the following values: $\sigma=3000$, $\sigma_2=500$, $\rho=4000$ and $\tau=0.00039$ (0.039%) with the step size for the angular rotation during formation of the X-ray diffraction profile being 0.9 arcseconds and the dynamic range being $10^4$ which is equivalent to that for measurements. As is typical for measurements the relevant information in the diffraction profile lies in a range of 400 arcseconds.

As an initial step, the influence of two of the parameters $\sigma_1$ and $\sigma_2$ was examined using the definition of the error E between the "measured" and calculated diffraction profiles given by the error equation 2) above.

Figure 9A:
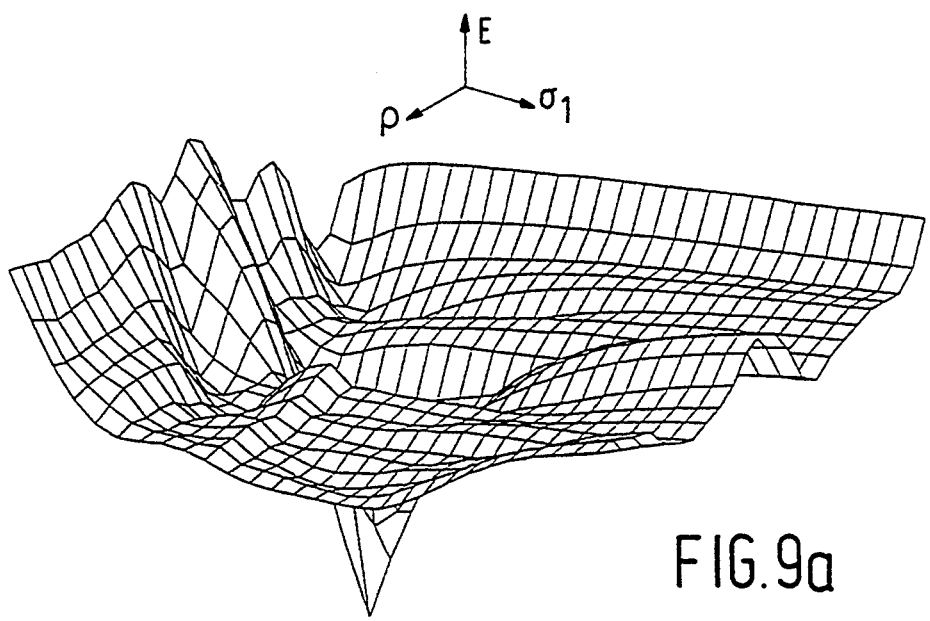
FIGS. 9a to c are schematic two-dimensional plots for illustrating the effect for two selected parameters which affect the strain profile on the error or difference between an artificial experimental X-ray diffraction profile obtained using the strain profile shown in FIG. 8 and a calculated X-ray diffraction profile with different degrees of smoothing using simulated annealing.
Figure 9B:
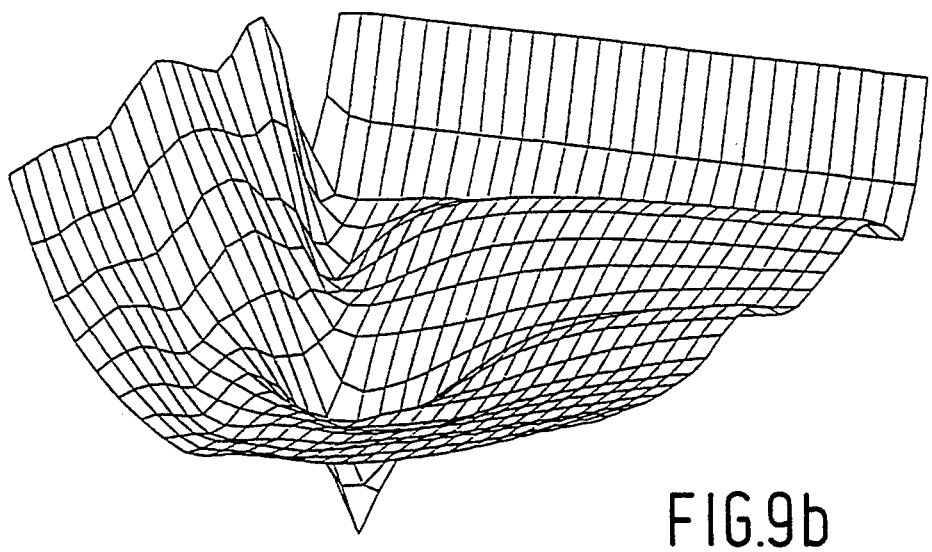
Figure 9C:
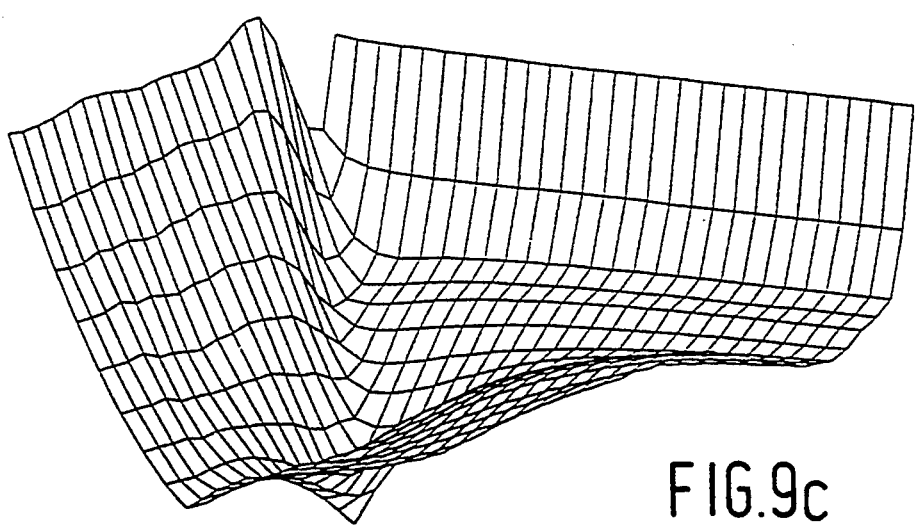

FIGS. 9a to 9c show two-dimensional plots of and p against the error E derived from the above error formula. FIG. 9a shows the error plot where the annealing curve with which the diffraction, n profiles are convoluted has a FWHM of 9 arcseconds while for FIG. 9b the FWHM for the annealing profile is 18 arcseconds and for FIG. 9c the FWHM is 90 arcseconds. As can clearly be seen in FIG. 9c the local minima in the error E have vanished leaving only one global minimum indicating that this annealing profile is, for this example, an appropriate first smoothing profile from which it is relatively simple for an optimization program to find this minimum which represents the best fit between the smoothed profiles.

Varying only two parameters in this case may be an oversimplification but the error plots shown in FIGS. 9a to 9c are intended only to indicate the situation and, as indicated above, the optimization process can be applied for all relevant parameters.

Figure 10:
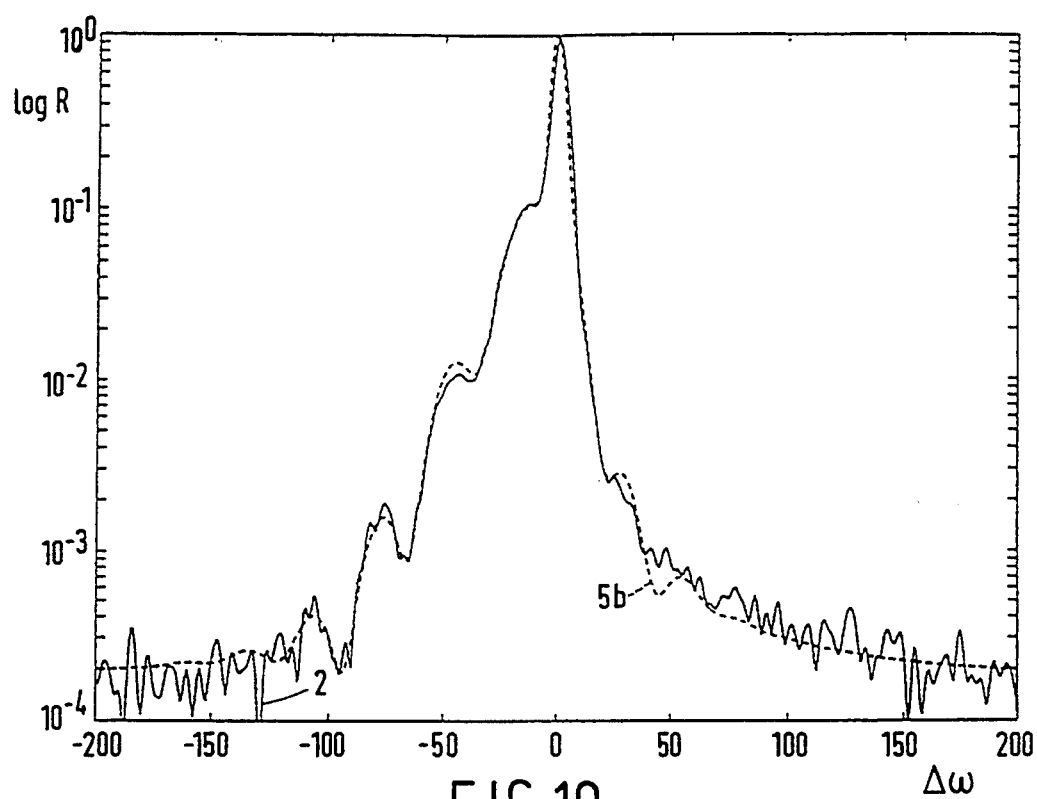
FIGS. 10 and 11 illustrate fitting results for two different experimental samples.
Figure 11:
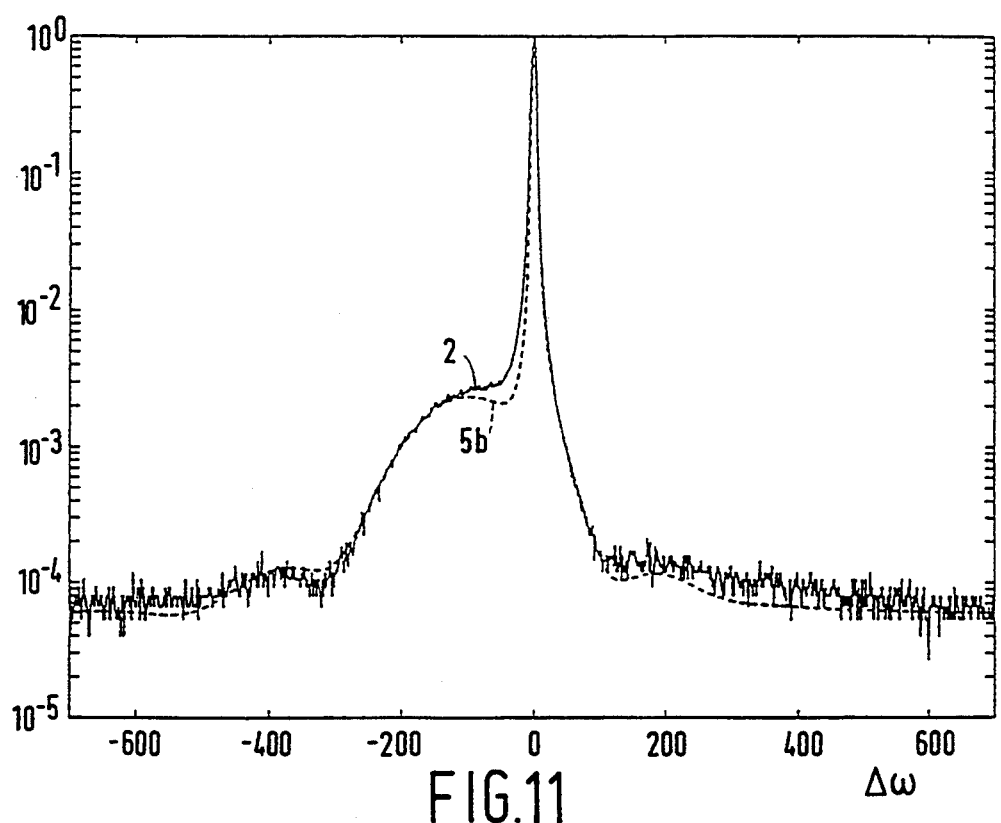

FIGS. 10 shows by means of the solid line the experimental X-ray profile 2 and by means of the dashed line the final adjusted calculated X-ray profile 5b for the 004 reflection for a (001) silicon wafer sample implanted with a dose of $5.10^{14}$ cm$^{-2}$ of phosphorus ions with an energy of 500 keV ( kilo electron volts). In this case the fitting procedure was carried out by first convoluting the diffraction profiles with a triangular annealing profile having a FWHM of 50 arcseconds enabling the maximum strain $\tau$ to be found easily and allowing the other parameters to be found without convolution. FIGS. 11 similarly shows by means of the solid line the experimental X-ray profile 2 and by means of the dashed line the final adjusted calculated X-ray profile 5b for the $026_1$ reflection for a (001) silicon wafer sample implanted with a dose of $5.10^{14}$ cm$^{-2}$ of boron ions with an energy of 45keV. In each case a good fit is achieved.

The fit achieved between the experimental and calculated X-ray diffraction profile profiles is influenced by the angular step size used in making the diffraction profile measurements and if this is too big the peak of the diffraction profile could be missed and result in a larger error in the measured peak intensity, especially if a four crystal monochromator is used because then the peak width is very narrow ( FWHM less than 8 arcseconds); however a step size of no greater than 0.9 arcseconds should avoid any such problems. If a larger step size has to be used, it should be possible to overcome this problem by interpolating the shape of the peak, for example assuming a Gaussian shape.

The present invention may be applied to problems other than ascertaining the strain profile of an ion-implanted semiconductor sample. Thus, for example, the described method may be applied with appropriate modification to the determination of the lattice mismatch between layers of a multi-layer structure the difficulties of which are described in, for example, a paper entitled "lattice mismatch of simple and complex structures by X-ray diffraction" by the present inventor published in "Heteroepitaxial approaches to semiconductors: lattice mismatch and its consequences" edited by A. T. Macrander and T. J. Drumrnond published in volume 89-5 of the proceedings of the electrochemistry society (1989). In addition, the present invention may be applied to the determination of layer thicknesses in such samples, both of which characteristics need to be monitored from the point of view of non-destructive quality control during production of semiconductor devices such as quantum well lasers or HEMTs or other microwave devices. The present invention may be applied to such cases in a manner similar to that described above but of course incorporating thickness and composition parameters, which may be correlated as described in the paper mentioned earlier in this paragraph.

The present invention may be applied to other forms of analysis, for example Auger Rutherford back scattering, secondary ion mass spectroscopy, X-ray photon spectroscopy, X-ray fluorescence spectroscopy, Mass spectroscopy, ultra violet and infra red spectroscopy and any other analysis techniques where a measured profile of a sample, which could be any suitable physical object, not necessarily man-made, is to be compared with a calculated profile to enable the extraction or determination of the values of selected parameters of the sample, which information may be used for, for example, quality control, optimisation of manufacturing processes and any other similar procedures.

From reading the present disclosure, other modifications and variations will be apparent to persons skilled in the art. Such modifications and variations may involve other features which are already known in the art and which may be used instead of or in addition to features already described herein. Although claims have been formulated in this application to particular combinations of features, it should be understood that the scope 01 the disclosure of the present application also includes any novel feature or combination of features disclosed herein either explicitly or implicitly, whether or not relating to the same invention as presently claimed in any claim and whether or not it mitigates any or all of the same technical problems as does the presently claimed invention. The applicants hereby give notice that new claims may be formulated to such features and/or combinations of such features during prosecution of the present application or of any further application derived therefrom.

I claim:

1. A method of determining a given characteristic of a material sample, which method comprises
    a) making measurements on the sample to obtain an experimental profile having structural features determined at least in part by the given characteristic,
    b) calculating an expected profile for the sample using selected parameters,
    c) applying a degree of smoothing to the experimental profile to reduce the structural features thereby producing a smoothed experimental profile,
    d) applying the same degree of smoothing to the calculated profile to produce a smoothed calculated profile,
    e) comparing the smoothed calculated profile with the smoothed experimental profile to determine the difference between the smoothed calculated profile and the smoothed experimental profile,
    f) modifying the calculated profile by varying at least one of the parameters until the smoothed modified calculated profile fits the smoothed experimental profile,
    g) repeating steps c) to f) using each time a degree of smoothing less than the previous time so that the structural features return and the final modified calculated profile provides a desired fit to the experimental profile thereby enabling the given characteristic to be determined from the parameters used for the final modified profile.

2. A method according to claim 1, which comprises making the measurements on the sample using a probe beam to obtain an experimental diffraction profile.

3. A method according to claim 1, which comprises making the measurements on the sample using X-ray analysis to obtain an experimental X-ray diffraction profile.

4. A method according to claim 1 which comprises providing the experimental and calculated profiles as normalised logarithmic profiles.

5. A method according to claim 1 which comprises comparing the profiles by determining the difference between corresponding points of the two profiles and summing these differences for a number of points to determine an error value for the difference between the experimental and calculated profiles.

6. A method according to claim 1 which comprises carrying out step f) each time by 1) varying the parameters in turn to determine which parameter causes the largest change in the difference between the experimental and calculated profiles, 2) varying that selected parameter until the change in the difference between the experimental and calculated profiles caused by varying that parameter reaches a predetermined limit, 3) storing the changed value of the selected parameter and repeating steps 1) to 3) for each parameter using the changed value of the selected parameter until a desired fit between the experimental and calculated profiles is achieved.

7. Using a method according to claim 1 to determine the strain profile of an ion-implanted semiconductor sample.

8. A method of determining a given characteristic of a material sample by X-ray analysis, which method comprises
    a) making X-ray measurements on the sample to obtain an experimental X-ray diffraction profile determined at least in part by the given characteristic,
    b) calculating an expected X-ray diffraction profile for the sample using selected parameters,
    c) applying a degree of smoothing to the experimental profile to reduce the structural features thereby producing a smoothed experimental profile, d) applying the same degree of smoothing to the calculated profile to produce a smoothed calculated profile.
e) comparing the smoothed calculated profile with the smoothed experimental profile to determine the difference between the smoothed calculated profile and the smoothed experimental profile,
f) modifying the calculated profile by varying at least one of the parameters until the smoothed modified calculated profile fits the smoothed experimental profile,
g) repeating steps c) to f) using each time a degree of smoothing less than the previous time so that the structural features return and the final modified calculated profile provides a desired fit to the experimental profile thereby enabling the given characteristic to be determined from the parameters used for the final modified profile.

9. Using a method according to claim 8 to determine the lattice mismatch between or composition of different layers of a multi-layer material sample.

10. A method according to claim 8, which comprises smoothing the experimental and calculated profiles by separately convoluting the profiles with a smoothing profile having a given base width and carrying out step g) by reducing the width of the smoothing profile each time steps c) to f) are repeated.

11. A method according to claim 10, which comprises smoothing the experimental and calculated profiles by convoluting each profile with a smoothing profile having the shape of a triangle of a given base width and carrying out step g) by reducing the base width of the triangle each time steps c) to f) are repeated until the smoothing profile is a delta function.

12. Using a method according to claim 11 to determine the thicknesses of the layers of a multi-layer material sample.

* * * * *